United States Patent
Fageon et al.

(10) Patent No.: US 9,233,056 B2
(45) Date of Patent: Jan. 12, 2016

(54) SOLID ANTI-SUN COMPOSITION BASED ON LIPOPHILIC ORGANIC UV SCREENING AGENT AND AEROGEL PARTICLES OF HYDROPHOBIC SILICA

(71) Applicant: L'OREAL, Paris (FR)

(72) Inventors: Laure Fageon, Paris (FR); Mathilde Lemal, Antony (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/355,425

(22) PCT Filed: Oct. 25, 2012

(86) PCT No.: PCT/EP2012/071142
§ 371 (c)(1),
(2) Date: Apr. 30, 2014

(87) PCT Pub. No.: WO2013/068236
PCT Pub. Date: May 16, 2013

(65) Prior Publication Data
US 2014/0294975 A1    Oct. 2, 2014

Related U.S. Application Data

(60) Provisional application No. 61/557,462, filed on Nov. 9, 2011.

(30) Foreign Application Priority Data

Nov. 7, 2011 (FR) ..................... 11 60059

(51) Int. Cl.
*A61K 8/02* (2006.01)
*A61K 8/25* (2006.01)
*A61K 8/35* (2006.01)
*A61K 8/37* (2006.01)
*A61K 8/49* (2006.01)
*A61K 8/58* (2006.01)
*A61Q 17/04* (2006.01)

(52) U.S. Cl.
CPC ............... *A61K 8/0225* (2013.01); *A61K 8/022* (2013.01); *A61K 8/0216* (2013.01); *A61K 8/0279* (2013.01); *A61K 8/25* (2013.01); *A61K 8/35* (2013.01); *A61K 8/37* (2013.01); *A61K 8/496* (2013.01); *A61K 8/4966* (2013.01); *A61K 8/585* (2013.01); *A61Q 17/04* (2013.01); *A61K 2800/262* (2013.01); *A61K 2800/412* (2013.01); *A61K 2800/522* (2013.01)

(58) Field of Classification Search
CPC .................. A61K 2800/262; A61K 2800/412; A61K 2800/522; A61K 8/0216; A61K 8/022; A61K 8/0225; A61K 8/0279; A61K 8/25; A61K 8/35; A61K 8/37; A61K 8/496; A61K 8/4966; A61K 8/585; A61Q 17/04
See application file for complete search history.

(56) References Cited

U.S. PATENT DOCUMENTS

| 6,146,617 A | 11/2000 | Kurz et al. |
| 2006/0177389 A1 | 8/2006 | Lott |
| 2009/0068255 A1 * | 3/2009 | Yu et al. ................. 424/450 |

FOREIGN PATENT DOCUMENTS

WO    WO 2007/078062 A1 *   7/2007   ............. A61Q 17/00

OTHER PUBLICATIONS

Product Information sheet for Dow Corning® VM-2270, Aerogel Fine Particles, (pp. 1-5, Jul. 12, 2007).*
Dow Corning, "Lucidity Anhydrous Sunscreen Gel", https://www.dowcorning.com/content/publishedlit/FORMUL_01312.pdf. Apr. 29, 2009.

* cited by examiner

*Primary Examiner* — Aradhana Sasan
(74) *Attorney, Agent, or Firm* — Novak Druce Connolly Bove + Quigg LLP

(57) ABSTRACT

The present invention thus relates to a solid composition, in particular in the form of a loose or compact powder, comprising, in a cosmetically acceptable medium: a) at least one pulverulent phase; b) at least one lipophilic organic UV screening agent characterized in that the pulverulent phase comprises at least aerogel particles of hydrophobic silica exhibiting a specific surface per unit of weight ($S_W$) ranging from 200 to 1500 m²/g, preferably from 600 to 1200 m²/g and better still from 600 to 800 m²/g, and a size, expressed as volume-average diameter (D[0.5]), of less than 1500 μm and preferably ranging from 1 to 30 μm, more preferably from 5 to 25 μm, better still from 5 to 20 μm and even better still from 5 to 15 μm. It also relates to a cosmetic method for caring for and/or making up human keratinous substances, in particular the skin of the body or of the face or the hair, comprising at least the application, to the surface of the keratinous substance, of at least one composition as defined above.

21 Claims, No Drawings

SOLID ANTI-SUN COMPOSITION BASED ON LIPOPHILIC ORGANIC UV SCREENING AGENT AND AEROGEL PARTICLES OF HYDROPHOBIC SILICA

CROSS REFERENCE TO RELATED APPLICATIONS

This application is a National Phase filing under 35 U.S.C. §371 of PCT/EP2012/071142 filed on Oct. 25, 2012; and this application claims priority to Application No. 1160059 filed in France on Nov. 7, 2011, and this application claims the benefit of U.S. Provisional Application No. 61/557,462 filed on Nov. 9, 2011; the entire contents of all are hereby incorporated by reference.

The present invention thus relates to a solid composition comprising, in a cosmetically acceptable medium:
a) at least one pulverulent phase
b) at least one lipophilic organic UV screening agent
characterized in that the pulverulent phase comprises at least aerogel particles of hydrophobic silica exhibiting a specific surface per unit of weight ($S_W$) ranging from 200 to 1500 m²/g, preferably from 600 to 1200 m²/g and better still from 600 to 800 m²/g, and a size, expressed as volume-average diameter (D[0.5]), of less than 1500 µm and preferably ranging from 1 to 30 µm, more preferably from 5 to 25 µm, better still from 5 to 20 µm and even better still from 5 to 15 µm.

It also relates to a cosmetic method for caring for and/or making up human keratinous substances, in particular the skin of the body or of the face or the hair, comprising at least the application, to the surface of the keratinous substance, of at least one composition as defined above.

It is known that radiation with wavelengths of between 280 nm and 400 nm makes possible tanning of the human epidermis and that radiation with wavelengths of between 280 and 320 nm, known under the name of UV-B rays, harms the development of a natural tan. Exposure is also capable of bringing about a detrimental change in the biomechanical properties of the epidermis which is reflected by the appearance of wrinkles, leading to premature ageing of the skin.

It is also known that UV-A rays with wavelengths of between 320 and 400 nm penetrate more deeply into the skin than UV-B rays. UV-A rays cause immediate and persistent browning of the skin. Daily exposure to UV-A rays, even of short duration, under normal conditions can result in damage to the collagen fibres and the elastin, which is reflected by a modification to the microrelief of the skin, the appearance of wrinkles and uneven pigmentation (liver spots, heterogeneity of the complexion).

Many cosmetic compositions intended for the photoprotection (UV-A and/or UV-B) of the skin have been provided to date. Formulations which provide the users with easy application on the skin are very particularly desired. These screening cosmetic compositions must moreover satisfy the regulations as regards protection factor and in particular the European regulations on anti-sun products, especially on the protection ratio between UV-B and UV-A radiation and more particularly the SPF/PPD ratio, which must be less than 3.

The efficacy of anti-sun compositions for UV-B protection is generally expressed by the sun protection factor (SPF), which is expressed mathematically by the ratio of the dose of UV radiation necessary to reach the erythemal threshold with the UV screening agent to the dose of UV radiation necessary to reach the erythemal threshold without UV screening agent. This factor thus concerns the efficacy of the protection having a spectrum of biological action centred in the UV-B range and consequently gives an account of the protection with regard to this UV-B radiation.

To characterize the protection with regard to UV-A radiation, the PPD (persistent pigment darkening) method, which measures the colour of the skin observed 2 to 4 hours after exposure of the skin to UV-A radiation, is particularly recommended and used. This method has been adopted since 1996 by the Japanese Cosmetic Industry Association (JCIA) as official test procedure for the UV-A labelling of products and is frequently used by test laboratories in Europe and the United States (Japan Cosmetic Industry Association Technical Bulletin. Measurement Standards for UVA protection efficacy. Issued Nov. 21, 1995 and effective as of Jan. 1, 1996).

The UV-$A_{PPD}$ sun protection factor (UV-Appd PF) is expressed mathematically by the ratio of the dose of UV-A radiation necessary to reach the pigmentation threshold with the UV screening agent (MPPDp) to the dose of UV-A radiation necessary to reach the pigmentation threshold without UV screening agent (MPPDnp).

$$UV\text{-}A_{PPD}PF = \frac{MPPDp}{MPPDnp}$$

Anti-sun compositions are fairly often provided in the form of an emulsion of oil-in-water type (that is to say, a cosmetically acceptable support consisting of a continuous aqueous dispersing phase and of a non-continuous oily dispersed phase) or of the water-in-oil type (that is to say, a cosmetically acceptable support consisting of a continuous oily dispersing phase and of a non-continuous aqueous dispersed phase) which comprises, at various concentrations, one or more conventional lipophilic and/or hydrophilic organic screening agents which are capable of selectively absorbing harmful UV rays, these screening agents (and their amounts) being selected as a function of the desired sun protection factor.

However, the incorporation of organic UV screening agents in this type of cosmetic composition sometimes results in an uncomfortable cosmetic feel, in particular a tacky effect during application to the skin, which persists over time. These cosmetic compositions comprising organic screening agents have a tendency to leave a glossy film at the surface of the skin.

The glossy effect contributed by the lipophilic organic UV screening agents increases in proportion as their content in the compositions increases; it is thus particularly high for the anti-sun compositions exhibiting high levels of SPF and PPD protection.

In the field of anti-sun cosmetics, the formulation form in the powder form makes it possible to avoid all these disadvantages due to the presence of fillers which make it possible to introduce softness and mattness. Loose or compact photoprotective powders based on inorganic UV screening agents which are metal oxide pigments, such as titanium dioxide or zinc oxide, are known in particular. The introduction of these inorganic screening agents into these formulation forms results in significant coverage and in a loss of the transparency of the product which leaves a whitening film on the skin.

There also exist, in Patent Application EP 0 839 518, cosmetic compositions in the loose or compact powder form comprising organic screening agents entrapped in a porous spherical silica aggregate. This type of product is less covering than the preceding one. Nevertheless, the content of screening agent which can be introduced into this type of formulation form remains low. For this reason, the efficacy (SPF) of this type of product remains limited.

The need thus remains to produce anti-sun cosmetic compositions, in the loose or compact powder form, which exhibit a high efficacy and which are transparent and non-covering on application.

The Applicant Company has discovered, surprisingly, that this objective can be achieved by using aerogel particles of hydrophobic silica in a solid composition based on lipophilic organic UV screening agents, in particular in a composition in the loose or compact powder form.

The present invention thus relates to a solid composition comprising, in a cosmetically acceptable medium:
a) at least one pulverulent phase
b) at least one lipophilic organic UV screening agent characterized in that the pulverulent phase comprises at least aerogel particles of hydrophobic silica exhibiting a specific surface per unit of weight ($S_W$) ranging from 200 to 1500 m²/g, preferably from 600 to 1200 m²/g and better still from 600 to 800 m²/g, and a size, expressed as volume-average diameter (D[0.5]), of less than 1500 μm and preferably ranging from 1 to 30 μm, more preferably from 5 to 25 μm, better still from 5 to 20 μm and even better still from 5 to 15 μm.

The compositions according to the invention are provided in particular in the form of a loose or compact powder.

It also relates to a cosmetic method for caring for and/or making up human keratinous substances, in particular the skin of the body or of the face or the hair, comprising at least the application, to the surface of the keratinous substance, of at least one composition as defined above.

The term "human keratinous substances" is understood to mean the skin (body, face, outline of the eyes), head of hair, eyelashes, eyebrows, body hair, nails, lips or mucous membranes.

The term "cosmetically acceptable medium" is understood to mean any medium compatible with the skin and/or its superficial body growths which exhibits a pleasant colour, a pleasant odour and a pleasant feel and which does not cause unacceptable discomfort (smarting, tightness, redness) liable to dissuade the consumer from using this composition.

The term "lipophilic organic UV screening agent" is understood to mean an organic molecule which is capable of screening out UV radiation between 290 and 400 nm and which can be dissolved in the molecular or dispersed state in an oily phase in order to obtain a macroscopically homogeneous phase. Mention may be made of the following examples of UV screening agents:

The term "organic molecule" is understood to mean any molecule comprising, in its structure, one or more carbon atoms.

Within the meaning of the present invention:
the term "solid" is intended to denote the state of the composition at ambient temperature (25° C.) and at atmospheric pressure (760 mmHg), that is to say a composition of high consistency, which retains its form during storage. In contrast to "fluid" compositions, it does not flow under its own weight. It is advantageously characterized by a hardness as defined below.
the term "compact powder" is intended to denote a mass of product, the cohesion of which is at least partly provided by virtue of a compacting during manufacture. In particular, by carrying out a measurement using a TA.XT. plus Texture Analyser sold by Stable Micro Systems, the compact powder according to the invention can advantageously exhibit a resistance to pressure of between 0.1 and 1 kg and in particular between 0.2 and 0.8 kg, with respect to the surface area of the spindle used (in the case in point, 7.07 mm²). This resistance is measured by causing an SMS P/3 flat-ended cylindrical spindle in contact with the powder to move over a distance of 2 mm at a speed of 0.5 mm/second; more generally, this powder is obtained by compacting. The term "compact powder" should be understood more specifically to mean that these powders exhibit a Shore A hardness, measured using a Zwick hardness tester, which varies, according to the intensity of the complexions under consideration, from 12 to 30° Shore A.
the term "loose powder" is intended to denote a mass of product which is capable of collapsing under its own weight, such a mass being formed of particles which are predominantly isolated and movable with respect to one another.

Aerogel Particles of Hydrophobic Silica

A composition according to the invention also comprises aerogel silica particles intended to stabilize the composition according to the invention by taking up a position at the dispersed phase/continuous phase interface.

Aerogels are ultralight porous materials which were first produced by Kristler in 1932.

They are generally synthesized by a sol-gel process in a liquid medium and then dried by extraction with a supercritical fluid. The supercritical fluid most commonly used is supercritical $CO_2$. This type of drying makes it possible to avoid shrinkage of the pores and of the material.

Other types of drying also make it possible to obtain porous materials starting from gel, namely (i) drying by freeze drying, which consists in solidifying the gel at low temperature and in then subliming the solvent, and (ii) drying by evaporation. The materials thus obtained are referred to respectively as cryogels and xerogels. The sol-gel process and the various drying operations are described in detail in Brinker C. J. and Scherer G. W., Sol-Gel Science, New York, Academic Press, 1990.

The term "hydrophobic silica" is understood to mean any silica whose surface is treated with silylating agents, for example halogenated silanes, such as alkylchlorosilanes, siloxanes, in particular dimethylsiloxanes, such as hexamethyldisiloxane, or silazanes, so as to functionalize the OH groups with silyl groups Si—Rn, for example trimethylsilyl groups.

The hydrophobic aerogel particles used in the present invention exhibit a specific surface per unit of weight ($S_W$) ranging from 200 to 1500 m²/g, preferably from 600 to 1200 m²/g and better still from 600 to 800 m²/g, and a size, expressed as volume-average diameter (D[0.5]), of less than 1500 μm and preferably ranging from 1 to 30 μm, more preferably from 5 to 25 μm, better still from 5 to 20 μm and even better still from 5 to 15 μm.

According to an advantageous embodiment, the hydrophobic aerogel particles used in the present invention have an oil absorption capacity, measured at the wet point, ranging from 5 to 18 ml/g, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste.

It is measured according to the "wet point" method or method for determining the oil uptake of a powder described in Standard NF T 30-022. It corresponds to the amount of oil adsorbed onto the available surface of the powder and/or absorbed by the powder by measurement of the wet point, described below:

An amount w=2 g of powder is placed on a glass plate and then the oil (isononyl isononanoate) is added dropwise. After addition of 4 to 5 drops of oil to the powder, mixing is carried out using a spatula, and addition of oil is continued until conglomerates of oil and powder have formed. From this point, the oil is added at the rate of one drop at a time and the mixture is subsequently triturated with the spatula. The addition of oil is stopped when a firm and smooth paste is obtained. This paste must be able to be spread over the glass plate without cracks or the formation of lumps. The volume Vs (expressed in ml) of oil used is then noted.

The oil uptake corresponds to the ratio Vs/w.

The aerogel particles of hydrophobic silica used according to the present invention are preferably aerogel particles of silylated silica (INCI name: silica silylate).

The preparation of aerogel particles of hydrophobic silica modified at the surface by silylation is further described in the document U.S. Pat. No. 7,470,725.

Use will in particular be made of aerogel particles of hydrophobic silica modified at the surface with trimethylsilyl groups.

The hydrophobic aerogel particles which can be used in the present invention advantageously exhibit a size, expressed as average diameter (D[0.5]), of less than 1500 µm and preferably ranging from 1 to 30 µm, preferably from 5 to 25 µm, better still from 5 to 20 µm and even better still from 5 to 15 µm.

The specific surface per unit of weight can be determined by the nitrogen absorption method, known as the BET (Brunauer-Emmett-Teller) method, described in The Journal of the American Chemical Society, Vol. 60, page 309, February 1938, which corresponds to International Standard ISO 5794/1 (appendix D). The BET specific surface corresponds to the total specific surface of the particles under consideration.

The sizes of the aerogel particles according to the invention can be measured by static light scattering using a commercial particle size analyser of MasterSizer 2000 type from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

According to an advantageous embodiment, the hydrophobic aerogel particles used in the present invention exhibit a specific surface per unit of weight ($S_W$) ranging from 600 to 800 m$^2$/g and a size, expressed as volume-average diameter (D[0.5]), ranging from 5 to 20 µm and better still from 5 to 15 µm.

The hydrophobic aerogel particles used in the present invention can advantageously exhibit a packed density p ranging from 0.04 g/cm$^3$ to 0.10 g/cm$^3$ and preferably from 0.05 g/cm$^3$ to 0.08 g/cm$^3$.

In the context of the present invention, this density can be assessed according to the following protocol, known as packed density protocol:

40 g of powder are poured into a graduated measuring cylinder and then the measuring cylinder is placed on a Stay 2003 device from Stampf Volumeter. The measuring cylinder is subsequently subjected to a series of 2500 packing actions (this operation is repeated until the difference in volume between two consecutive tests is less than 2%) and then the final volume Vf of packed powder is measured directly on the measuring cylinder.

The packed density is determined by the ratio weight(w)/Vf, in the case in point 40/Vf (Vf being expressed in cm$^3$ and w in g).

According to one embodiment, the hydrophobic aerogel particles used in the present invention exhibit a specific surface per unit of volume $S_V$ ranging from 5 to 60 m$^2$/cm$^3$, preferably from 10 to 50 m$^2$/cm$^3$ and better still from 15 to 40 m$^2$/cm$^3$.

The specific surface per unit of volume is given by the relationship: $S_V = S_W * \rho$, where $\rho$ is the packed density, expressed in g/cm$^3$, and $S_W$ is the specific surface per unit of weight, expressed in m$^2$/g, as defined above.

Mention may be made, as hydrophobic silica aerogels which can be used in the invention, for example, of the aerogel sold under the name VM-2260 (INCI name: Silica silylate) by Dow Corning, the particles of which exhibit an average size of approximately 1000 microns and a specific surface per unit of weight ranging from 600 to 800 m$^2$/g.

Mention may also be made of the aerogels sold by Cabot under the references Aerogel TLD 201, Aerogel OGD 201 and Aerogel TLD 203, Enova Aerogel MT 1100 and Enova Aerogel MT 1200.

Use will more particularly be made of the aerogel sold under the name VM-2270 (INCI name: Silica silylate) by Dow Corning, the particles of which exhibit an average size ranging from 5 to 15 microns and a specific surface per unit of weight ranging from 600 to 800 m$^2$/g.

The silica aerogel particles in accordance with the invention are preferably present in the cosmetic composition in an amount of active material ranging from 0.5% to 15% by weight and more preferentially from 1% to 10% by weight relative to the total weight of the composition.

Particulate Phase

The pulverulent phase according to the present invention preferably comprises at least one additional filler, that is to say, in addition to the aerogel particles of hydrophobic silica, the composition preferably comprises at least one filler other than the aerogel particles.

As specified above, the solid composition according to the invention comprises a pulverulent phase preferably at a content of greater than or equal to 15% by weight, in particular of greater than or equal to 40% by weight and more particularly ranging from 50% to 99.9% by weight, with respect to the total weight of the said composition.

Within the meaning of the present invention, this pulverulent phase is formed of any particulate solid material present in the composition and in particular fillers and/or colorants, such as, for example, pigments.

Thus, the pulverulent phase comprises, in addition to the aerogel particles of hydrophobic silica, at least one additional filler and optionally at least one colorant.

Additional Fillers

The term "fillers" should be understood as meaning colourless or white and inorganic or synthetic particles of any shape which are insoluble and dispersed in the medium of the composition, whatever the temperature at which the composition is manufactured.

Inorganic or organic in nature, they make it possible to confer, on the composition, softness, mattness and uniformity on the skin.

The additional fillers used in the compositions according to the present invention can be in lamellar (or platelet) form, in spherical (or globular) form, in the form of fibres or in any other intermediate form between these defined forms.

In the present patent application, the term "spherical particles" is understood to mean particles which have the shape or substantially the shape of a sphere and which are insoluble in the medium of the composition according to the invention, even at the melting point of the medium (approximately 100° C.).

In addition, the term "lamellar particles" is understood here to mean particles of parallelepipedal shape (rectangular or square surface), discoid shape (circular surface) or ellipsoid shape (oval surface) characterized by three dimensions: a length, a width and a height, which particles are insoluble in the medium of the composition according to the invention, even at the melting point of the medium (approximately 100° C.).

According to a particularly preferred form of the invention, the pulverulent phase comprises, as additional fillers, a mixture of spherical particles and lamellar particles.

Spherical Particles

The spherical particles used according to the invention have the shape or substantially the shape of a sphere and can be hollow or solid. Advantageously, the particles of the invention have a particle size (number-average diameter) ranging from 0.1 µm to 250 µm, better still ranging from 1 µm to 150 µm and better still from 10 µm to 100 µm.

The spherical particles can be organic or inorganic microspheres. Mention may be made, as spherical organic powders, for example, of polyamide powders and in particular Nylon® powders, such as Nylon-1 or Polyamide 12, sold under the Orgasol names by Atochem; polyethylene powders; polytetrafluoroethylene (Teflon®) powders; microspheres based on acrylic copolymers, such as those made of ethylene glycol dimethacrylate/lauryl methacrylate copolymer sold by Dow Corning under the Polytrap name; expanded powders, such as hollow microspheres and in particular the microspheres sold under the Expancel name by Kemanord Plast or under the name Micropearl F 80 ED by Matsumoto; silicone resin microbeads, such as those sold under the Tospearl name by Toshiba Silicone; polymethyl methacrylate microspheres, sold under the name Microsphere M-100 by Matsumoto or under the name Covabead LH85 by Wackherr; ethylene/acrylate copolymer powders, such as those sold under the Flobeads name by Sumitomo Seika Chemicals; powders formed of natural organic materials, such as starch powders, in particular powders formed of maize, wheat or rice starch, which are or are not crosslinked, such as powders formed of starch crosslinked with octenylsuccinic anhydride, sold under the Dry-Flo name by National Starch; metal soaps derived from organic carboxylic acids having from 8 to 22 carbon atoms, preferably from 12 to 18 carbon atoms, for example zinc stearate, magnesium stearate, lithium stearate, zinc laurate or magnesium myristate; Polypore® L 200 (Chemdal Corporation); silicone resin microbeads (Tospearl® from Toshiba, for example); polyurethane powders, in particular powders formed of crosslinked polyurethane comprising a copolymer, the said copolymer comprising trimethylol hexyllactone, such as the hexamethylene diisocyanate/trimethylol hexyllactone polymer sold under the name Plastic Powder D-400® or Plastic Powder D-800® by Toshiki; carnauba microwaxes, such as that sold under the name MicroCare 350® by Micro Powders; synthetic wax microwaxes, such as that sold under the name MicroEase 114S® by Micro Powders; microwaxes composed of a mixture of carnauba wax and polyethylene wax, such as those sold under the names Micro Care 300® and 310® by Micro Powders; microwaxes consisting of a mixture of carnauba wax and synthetic wax, such as that sold under the name Micro Care 325® by Micro Powders; or polyethylene microwaxes, such as those sold under the names Micropoly 200®, 220®, 220L® and 250S® by Micro Powders.

According to a particularly preferred embodiment of the present invention, the spherical particles will be chosen from polyamide powders, polymethyl methacrylate microspheres, polytetrafluoroethylene powders and their mixtures.

These spherical particles can be present in amounts preferably ranging from 20% to 100% by weight, more preferentially from 20% to 50% by weight and more particularly from 25% to 35% by weight, with respect to the total weight of the mixture of spherical particles and lamellar particles.

Lamellar Particles

As indicated above, lamellar particles are particles of parallelepipedal shape (rectangular or square surface), discoid shape (circular surface) or ellipsoid shape (oval surface), characterized by three dimensions: a length, a width and a height. When the shape is circular, the length and the width are identical and correspond to the diameter of a disc, whereas the height corresponds to the thickness of the disc. When the surface is oval, the length and the width correspond, respectively, to the large axis and the small axis of an ellipse and the height corresponds to the thickness of the elliptic disc formed by the platelet. When it is a parallelepiped, the length and the width can be of identical or different dimensions: when they are of the same dimension, the shape of the surface of the parallelepiped is square; in the contrary case, the shape is rectangular. With regard to the height, it corresponds to the thickness of the parallelepiped.

The length of the lamellar particles used according to the invention preferably ranges from 0.01 to 100 µm, better still from 0.1 to 50 µm and even better still from 1 to 50 µm. The width of these platelets preferably ranges from 0.01 to 100 µm, better still from 0.1 to 50 µm and even better still from 1 to 10 µm. The height (thickness) of these platelets preferably ranges from 0.1 nm to 1 µm (0.1 to 1000 nm), better still from 1 nm to 600 nm and even better still from 1 nm to 500 nm. Mention may be made, as lamellar particles which can be used in the composition of the invention, of lamellar silicates.

Mention may be made, as lamellar silicates, of talcs, micas, perlites and their mixtures.

Talcs are hydrated magnesium silicates usually comprising aluminium silicate. The crystal structure of talc consists of repeated layers of a sandwich of brucite between layers of silica.

Micas are aluminium silicates optionally comprising iron and/or alkali metals. They have the property of being able to split up into thin layers (approximately 1 µm). They generally have a dimension ranging from 5 to 150 µm, preferably from 10 to 100 µm and better still from 10 to 60 µm for the largest dimension (length) and a height (thickness) of from 0.1 to 0.5 µm. Mention may be made, as micas, of phlogopite, muscovite, fluorophlogopite, vermiculite and their mixtures.

Mention may also be made, among lamellar silicates, of perlites and preferably expanded perlites.

The perlites which can be used according to the invention are generally aluminosilicates of volcanic origin and have the composition:

70.0-75.0% by weight of silica $SiO_2$
12.0-15.0% by weight of aluminium oxide $Al_2O_3$
3.0-5.0% of sodium oxide $Na_2O$
3.0-5.0% of potassium oxide $K_2O$
0.5-2% of iron oxide $Fe_2O_3$→
0.2-0.7% of magnesium oxide $MgO$
0.5-1.5% of calcium oxide $CaO$
0.05-0.15% of titanium oxide $TiO_2$ The perlite is ground, dried and then calibrated in a first stage. The product obtained, known as perlite ore, is grey-coloured and has a size of the order of 100 µm.

The perlite ore is subsequently expanded (1000° C./2 seconds) to give more or less white particles. When the temperature reaches 850-900° C., the water trapped in the structure of the material evaporates and brings about the expansion of the material, with respect to its original volume. The expanded perlite particles in accordance with the invention may be obtained via the expansion process described in U.S. Pat. No. 5,002,698.

Preferably, the perlite particles used will be ground; in this case, they are known as Expanded Milled Perlite (EMP). They preferably have a particle size defined by a median diameter $D_{50}$ ranging from 0.5 to 50 μm and preferably from 0.5 to 40 μm.

Preferably, the perlite particles used exhibit a loose bulk density at 25° C. ranging from 10 to 400 kg/m$^3$ (Standard DIN 53468) and preferably from 10 to 300 kg/m$^3$. Preferably, the expanded perlite particles according to the invention have a water absorption capacity, measured at the wet point, ranging from 200% to 1500% and preferably from 250% to 800%.

The wet point corresponds to the amount of water which has to be added to 1 g of particle in order to obtain a homogeneous paste. This method derives directly from the oil uptake method applied to solvents. The measurements are carried out in the same way via the wet point and the flow point, which have, respectively, the following definitions:
wet point: weight, expressed in grams per 100 g of product, corresponding to the production of a homogeneous paste during the addition of a solvent to a powder;
flow point: weight, expressed in grams per 100 g of product, at and above which the amount of solvent is greater than the ability of the powder to retain it. This is reflected by the production of a more or less homogeneous mixture which flows over the glass plate.

The wet point and the flow point are measured according to the following protocol:

According to a particularly preferred embodiment of the present invention, the lamellar particles will be chosen from an expanded perlite, a talc, a mica and their mixtures.

Advantageously, use is more particularly made, in the composition of the invention, as lamellar particles, of talc, such as the products sold under the names Rose Talc and Talc SG-2000 by Nippon Talc; mica, such as the products sold under the names Mica M RP and Silk Mica by the company Merck; titanium oxide-coated micas, such as mica/titanium oxide/brown iron oxide (CTFA name: Mica/Iron oxides/Titanium dioxide), sold under the name Cloisonne Rouge Flambe 440× by Engelhard; or expanded perlite (INCI name: Expanded Milled Perlite), as sold under the name Optimat 1430 OR by World Minerals.

These lamellar particles can be present in amounts preferably ranging from 40% to 100% by weight, more preferentially from 50% to 91% by weight and better still from 60% to 80% by weight, with respect to the total weight of the mixture of spherical particles and lamellar particles.

Mention may also be made, among the additional fillers which can be present in the pulverulent phase of the composition, of fibres, such as fibres of synthetic or natural and inorganic or organic origin. They can be short or long, individual or organized, for example braided, and hollow or solid. They can have any shape and can in particular be circular or polygonal (square, hexagonal or octagonal) in cross section, depending on the specific application envisaged. In particular, their ends are blunted and/or polished to prevent injury. The fibres have a length ranging from 1 μm to 10 mm, preferably from 0.1 mm to 5 mm and better still from 0.3 mm to 3 mm. Their cross section may be included in a circle with a diameter ranging from 2 nm to 500 μm, preferably ranging from 100 nm to 100 μm and better still ranging from 1 μm to 50 μm. Mention may be made, as fibres which can be used in the compositions according to the invention, of non-rigid fibres, such as polyamide fibres, such as in particular Nylon (or Polyamide 6) (INCI name: Nylon 6) fibres or Nylon 6,6 (or Polyamide 66) (INCI name: Nylon 66) fibres, or rigid fibres, such as polyimide/amide fibres, for example those sold under the Kermel® or Kermel Tech® names by Rhodia, or poly(p-phenylene terephthalamide) (or aramid) fibres, sold in particular under the Kevlar® name by DuPont de Nemours, and their mixtures.

The pulverulent phase can additionally comprise colouring agents.

Colouring Agent(s)

The compositions according to the invention can also comprise colouring agents.

The colouring agent(s) or colorant(s) according to the invention is (or are) preferably chosen from pigments, pearlescent agents, water-soluble or fat-soluble dyes, and their mixtures.

Pigments

The term "pigments" should be understood as meaning white or coloured and inorganic or organic particles of any shape which are insoluble in the physiological medium and which are intended to colour the composition.

The pigments can be white or coloured and inorganic and/or organic.

Mention may be made, among the inorganic pigments, of titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, such as aluminium powder or copper powder.

The organic pigments can be chosen from the materials below and their mixtures: cochineal carmine,
organic pigments of azo dyes, anthraquinone dyes, indigoid dyes, xanthene dyes, pyrene dyes, quinoline dyes, triphenylmethane dyes or fluoran dyes.

Mention may in particular be made, among the organic pigments, of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5 or FD&C Yellow No. 6.

The chemical substances corresponding to each of the organic colorants cited above are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by reference.

A composition according to the invention can comprise a content of pigments ranging from 0% to 30% by weight, with respect to the total weight of the composition, preferably ranging from 2% to 20% by weight and preferentially ranging from 4% to 10% by weight, with respect to the total weight of the composition.

Pearlescent Agents

The term "pearlescent agents" should be understood as meaning coloured particles of any shape, which are or are not iridescent, produced in particular by certain molluscs in their shells or else synthesized, and which exhibit a colour effect via optical interference.

Mention may be made, as examples of pearlescent agents, of pearlescent pigments, such as titanium oxide-coated mica covered with an iron oxide, mica covered with bismuth oxychloride or titanium oxide-coated mica covered with chromium oxide, or pearlescent pigments based on bismuth oxychloride. They can also be mica particles, at the surface of which are superimposed at least two successive layers of metal oxides and/or of organic colorants.

The compositions according to the invention can comprise a content of pearlescent agents ranging from 0% to 30% by weight, for example from 0.01% to 5% by weight, with respect to the total weight of the composition.

In addition to the fillers and pigments, the particulate phase of the invention can comprise water-soluble or fat-soluble dyes.

The term "fat-soluble dyes" should be understood as meaning compounds, generally organic, which are soluble in fatty substances, such as oils.

The fat-soluble dyes are, for example, Sudan red, D&C Red No. 17, D&C Green No. 6, β-carotene, soybean oil, Sudan brown, D&C Yellow No. 11, D&C Violet No. 2, D&C Orange No. 5, quinoline yellow, annatto or bromo acids.

Within the meaning of the invention, the term "water-soluble dye" is understood to mean any natural or synthetic compound, generally organic, which is soluble in an aqueous phase or in water-miscible solvents and which is suitable for colouring.

Mention may in particular be made, as water-soluble dyes suitable for the invention, of synthetic or natural water-soluble dyes, such as, for example, FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanin (beetroot), carmine, copper chlorophyllin, methylene blue, anthocyanins (oenocyanin, black carrot, hibiscus, elder), caramel and riboflavin.

Liquid Fatty Phase

According to a specific form of the invention, the compositions in accordance with the invention can comprise at least one liquid fatty phase.

This fatty phase can advantageously be used as binder in the said pulverulent phase.

The term "liquid" is understood to mean liquid at room temperature (25° C.) and atmospheric pressure (760 mmHg).

The liquid fatty phase generally comprises, in addition to the lipophilic UV screening agent or agents, at least one volatile or non-volatile hydrocarbon oil and/or one volatile or non-volatile silicone oil.

Within the meaning of the invention, the term "volatile oil" is understood to mean an oil which is capable of evaporating on contact with the skin or the keratinous fibre in less than one hour, at ambient temperature and atmospheric pressure. The volatile oil(s) of the invention are volatile cosmetic oils which are liquid at ambient temperature and which have a non-zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" is understood to mean an oil which remains on the skin or the keratinous fibre, at ambient temperature and atmospheric pressure, for at least several hours and which has in particular a vapour pressure of less than $10^{-3}$ mmHg (0.13 Pa).

a) Hydrocarbon Oils

Mention may in particular be made, as non-volatile hydrocarbon oils which can be used according to the invention, of:

(i) hydrocarbon oils of vegetable origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, maize oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkinseed oil, cucumber oil, blackcurrant oil, evening primrose oil, millet oil, barley oil, quinoa oil, rye oil, safflower oil, candlenut oil, passionflower oil and musk rose oil; or else caprylic/capric acid triglycerides, such as those sold by Stéarineries Dubois or those sold under the names Miglyol 810, 812 and 818 by Dynamit Nobel, (ii) synthetic ethers having from 10 to 40 carbon atoms;

(iii) linear or branched hydrocarbons of mineral or synthetic origin, such as petrolatum, polydecenes, hydrogenated polyisobutene, such as Parleam, squalane and their mixtures;

(iv) synthetic esters, such as the oils of formula RCOOR' in which R represents the residue of a linear or branched fatty acid comprising from 1 to 40 carbon atoms and R' represents a hydrocarbon chain, in particular a branched hydrocarbon chain, comprising from 1 to 40 carbon atoms, provided that R+R'≥10, such as, for example, purcellin oil (cetearyl octanoate), isopropyl myristate, isopropyl palmitate, $C_{12}$-$C_{15}$ alkyl benzoate, such as the product sold under the trade name Finsolv TN or Witconol TN by Witco or Tegosoft TN by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, alcohol or polyalcohol octanoates, decanoates or ricinoleates, such as propylene glycol dioctanoate; hydroxylated esters, such as isostearyl lactate or diisostearyl malate; and pentaerythritol esters; citrates or tartrates, such as linear di($C_{12}$-$C_{13}$ alkyl) tartrates, such as those sold under the name Cosmacol ETI by Enichem Augusta Industriale, and also linear di($C_{14}$-$C_{15}$ alkyl) tartrates, such as those sold under the name Cosmacol ETL by the same company; acetates;

(v) fatty alcohols which are liquid at ambient temperature and which have a branched and/or unsaturated carbon chain comprising from 12 to 26 carbon atoms, such as octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC by Cognis;

(viii) fatty amides, such as isopropyl N-lauroyl sarcosinate, such as the product sold under the trade name Eldew SL205 from Ajinomoto;

and their mixtures.

Mention may in particular be made, as volatile hydrocarbon oils which can be used according to the invention, of hydrocarbon oils having from 8 to 16 carbon atoms, in particular branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, or the alkanes described in the patent applications from Cognis, WO 2007/068371 or WO 2008/155059 (mixtures of different alkanes differing by at least one carbon). These alkanes are obtained from fatty alcohols, themselves obtained from coconut oil or palm oil, the oils sold under the Isopar or Permethyl trade names, branched $C_8$-$C_{16}$ esters, isohexyl neopentanoate and their mixtures.

Other volatile hydrocarbon oils, such as petroleum distillates, in particular those sold under the name Shell Solt by Shell, can also be used. According to one embodiment, the volatile solvent is chosen from volatile hydrocarbon oils having from 8 to 16 carbon atoms and their mixtures.

b) Silicone Oils

The non-volatile silicone oils can be chosen in particular from non-volatile polydimethylsiloxanes (PDMSs), polydimethylsiloxanes comprising alkyl or alkoxy groups which are pendent and/or at the end of the silicone chain, which groups each have from 2 to 24 carbon atoms, or phenylated silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Mention may be made, as volatile silicone oils, for example, of volatile linear or cyclic silicone oils, in particular those having a viscosity≤8 centistokes ($8×10^{-6}$ $m^2$/s) and having in particular from 2 to 7 silicon atoms, these silicones optionally comprising alkyl or alkoxy groups having from 1 to 10 carbon atoms. Mention may in particular be made, as volatile silicone oil which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and their mixtures.

Mention may also be made of volatile linear alkyltrisiloxane oils of general formula (I):

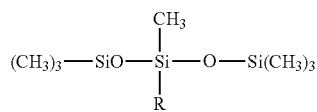

where R represents an alkyl group comprising from 2 to 4 carbon atoms, one or more hydrogen atoms of which can be replaced by a fluorine or chlorine atom.

Mention may be made, among the oils of general formula (I), of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is respectively a butyl group, a propyl group or an ethyl group.

According to a specific embodiment, the liquid fatty phase can comprise one or more liquid lipophilic screening agents and in particular can consist solely of the said liquid lipophilic UV screening agent or agents.

The term "liquid" is understood to mean liquid at room temperature (25° C.) and atmospheric pressure (760 mmHg).

The liquid fatty phase preferably varies from 0.1% to 85% by weight and preferably from 5% to 50% by weight, with respect to the total weight of the composition.

Lipophilic Organic Screening Agents

The lipophilic organic UV screening agents are chosen in particular from cinnamic derivatives; anthranilates; salicylic derivatives; dibenzoylmethane derivatives, camphor derivatives; benzophenone derivatives; β,β-diphenylacrylate derivatives; triazine derivatives; benzotriazole derivatives; benzalmalonate derivatives, in particular those mentioned in U.S. Pat. No. 5,624,663; imidazolines; p-aminobenzoic acid (PABA) derivatives; benzoxazole derivatives, such as described in Patent Applications EP 0 832 642, EP 1 027 883, EP 1 300 137 and DE 101 62 844; screening polymers and screening silicones, such as those described in particular in Patent Application WO 93/04665; dimers derived from α-alkylstyrene, such as those described in Patent Application DE 198 55 649; 4,4-diarylbutadienes, such as described in Patent Applications EP 0 967 200, DE 197 46 654, DE 197 55 649, EP-A-1 008 586, EP 1 133 980 and EP 133 981; merocyanine derivatives, such as those described in Patent Applications WO 04/006 878, WO 05/058 269, WO 06/032 741, FR 2 957 249 and FR 2 957 250; and their mixtures.

Mention may be made, as examples of additional organic photoprotective agents, of those denoted hereinbelow under their INCI names:

Mention may be made, as examples of lipophilic organic UV screening agents, of those denoted hereinbelow under their INCI names:

Dibenzoylmethane Derivatives:
Butyl Methoxy Dibenzoylmethane or avobenzone, provided for sale under the trade name Parsol 1789 by DSM Nutritional Products,
Para-Aminobenzoic Acid Derivatives:
PABA,
Ethyl PABA,
Ethyl Dihydroxypropyl PABA,
Ethylhexyl Dimethyl PABA, sold in particular under the name Escalol 507 by ISP,
Salicylic Derivatives:
Homosalate, sold under the name Eusolex HMS by Rona/EM Industries,
Ethylhexyl Salicylate, sold under the name Neo Heliopan OS by Symrise,
Cinnamic Derivatives:
Ethylhexyl Methoxycinnamate, sold in particular under the trade name Parsol MCX by DSM Nutritional Products,
Isopropyl Methoxycinnamate,
Isoamyl Methoxycinnamate, sold under the trade name Neo Heliopan E 1000 by Symrise,
Cinoxate,
Diisopropyl Methylcinnamate,
β,β-Di phenylacrylate Derivatives:
Octocrylene, sold in particular under the trade name Uvinul N539 by BASF,
Etocrylene, sold in particular under the trade name Uvinul N35 by BASF,
Benzophenone Derivatives:
Benzophenone-1, sold under the trade name Uvinul 400 by BASF,
Benzophenone-2, sold under the trade name Uvinul D50 by BASF,
Benzophenone-3 or Oxybenzone, sold under the trade name Uvinul M40 by BASF,
Benzophenone-6, sold under the trade name Helisorb 11 by Norquay,
Benzophenone-8, sold under the trade name Spectra-Sorb UV-24 by American Cyanamid,
Benzophenone-12,
n-Hexyl 2-(4-diethylamino-2-hydroxybenzoyl)benzoate, sold under the trade name Uvinul A+ or, in the form of a mixture with octyl methoxycinnamate, under the trade name Uvinul A+B by BASF,
1,1'-(1,4-piperazinediyl)bis[1-[2-[4-(diethylamino)-2-hydroxybenzoyl]phenyl]methanone (CAS 919803-06-8), in its micronized or non-micronized form, Benzylidenecamphor Derivatives:
3-Benzylidene Camphor, manufactured under the name Mexoryl SD by Chimex,
4-Methylbenzylidene Camphor, sold under the name Eusolex 6300 by Merck, Polyacrylamidomethyl Benzylidene Camphor, manufactured under the name Mexoryl SW by Chimex,
Phenylbenzotriazole Derivatives:
Drometrizole Trisiloxane, sold under the name Silatrizole by Rhodia Chimie,
Triazine Derivatives:
Bis-Ethylhexyloxyphenol Methoxyphenyl Triazine, sold under the trade name Tinosorb S by BASF,
Ethylhexyl Triazone, sold in particular under the trade name Uvinul T150 by BASF,
Diethylhexyl Butamido Triazone, sold under the trade name Uvasorb HEB by Sigma 3V,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
Anthranilic Derivatives:
Menthyl Anthranilate, sold under the trade name Neo Heliopan MA by Symrise,
Imidazoline Derivatives:
Ethylhexyl Dimethoxybenzylidene Dioxoimidazoline Propionate,
Benzalmalonate Derivatives:
Dineopentyl 4'-methoxybenzalmalonate,
Polyorganosiloxane comprising benzalmalonate functional groups, such as Polysilicone-15, sold under the trade name Parsol SLX by DSM,
4,4-Diarylbutadiene Derivatives:
1,1-Dicarboxy(2,2'-dimethylpropyl)-4,4-diphenylbutadiene,
Benzoxazole Derivatives:
2,4-Bis[4-[5-(1,1-dimethylpropyl)benzoxazol-2-yl]phenylimino]-6-[(2-ethylhexyl)imino]-1,3,5-triazine, sold under the name Uvasorb K2A by Sigma 3V, and their mixtures.
Lipophilic Merocyanine Derivatives:
Octyl 5-N,N-diethylamino-2-phenylsulfonyl-2,4-pentadienoate
and their mixtures.
The preferred lipophilic or insoluble organic screening agents are chosen from:
Butyl Methoxy Dibenzoylmethane,
Ethylhexyl Methoxycinnamate,
Ethylhexyl Salicylate,
Homosalate,
Butyl Methoxy Dibenzoylmethane,
Octocrylene,
Benzophenone-3,
n-Hexyl 2-(4-diethylamino-2-hydroxybenzoyl)benzoate,
4-Methylbenzylidene Camphor,
Bis-Ethylhexyloxyphenol Methoxyphenyl Triazine,
Ethylhexyl Triazone,
Diethylhexyl Butamido Triazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4,6-Tris(biphenyl-4-yl)-1,3,5-triazine,
2,4,6-Tris(terphenyl)-1,3,5-triazine,
Drometrizole Trisiloxane
Polysilicone-15,
1,1-Dicarboxy(2,2'-dimethylpropyl)-4,4-diphenylbutadiene,
2,4-Bis[4-[5-(1,1-dimethylpropyl)benzoxazol-2-yl]phenylimino]-6-[(2-ethylhexyl)imino]-1,3,5-triazine,
and mixtures thereof.

The preferred lipophilic organic screening agents are more particularly chosen from:
Butyl Methoxy Dibenzoylmethane,
Octocrylene,
Ethylhexyl Salicylate,
n-Hexyl 2-(4-diethylamino-2-hydroxybenzoyl)benzoate,
Bis-Ethylhexyloxyphenol Methoxyphenyl Triazine,
Ethylhexyl Triazone,
Diethylhexyl Butamido Triazone,
Drometrizole Trisiloxane, and their mixtures.

The lipophilic organic UV screening agent or agents are preferably present in the compositions according to the invention at a content ranging from 0.1% to 40% by weight and in particular from 5% to 25% by weight, with respect to the total weight of the composition.

Polyols

According to a specific form of the invention, the solid anhydrous composition according to the invention comprises at least one $C_2$-$C_{32}$ polyol.

This compound is particularly advantageous for conferring an affinity for water on the solid anhydrous composition in which it is present.

The term "polyol" should be understood as meaning, within the meaning of the present invention, any organic molecule comprising at least two free hydroxyl groups.

Preferably, a polyol in accordance with the present invention is present in liquid form at ambient temperature.

A polyol suitable for the invention can be a compound of saturated or unsaturated and linear, branched or cyclic alkyl type carrying, on the alkyl chain, at least two —OH functional groups, in particular at least three —OH functional groups and more particularly at least four —OH functional groups.

The polyols advantageously suitable for the formulation of a composition according to the present invention are those exhibiting in particular from 2 to 32 carbon atoms and preferably from 3 to 16 carbon atoms.

Advantageously, the polyol can be chosen, for example, from ethylene glycol, pentaerythritol, trimethylolpropane, propylene glycol, 1,3-propanediol, butylene glycol, isoprene glycol, pentylene glycol, hexylene glycol, glycerol, polyglycerols, such as glycerol oligomers, for example diglycerol, polyethylene glycols and their mixtures.

According to a preferred embodiment of the invention, the said polyol is chosen from ethylene glycol, pentaerythritol, trimethylolpropane, propylene glycol, glycerol, polyglycerols, polyethylene glycols and their mixtures.

The polyol or polyols are preferably present in an amount ranging from 0.1% to 20% by weight and better still from 0.1% to 10% by weight, with respect to the total weight of the said composition.

Aqueous Phase

According to a specific form of the invention, the composition according to the invention can comprise an aqueous phase.

This aqueous phase, when present, is employed in an amount compatible with the pulverulent formulation form required according to the invention.

The aqueous phase can be a demineralized water or alternatively a floral water, such as cornflower water, and/or a mineral water, such as Vittel water, Lucas water or La Roche-Posay water, and/or a thermal water.

The aqueous phase can also comprise a polyol which is miscible with water at ambient temperature (25° C.) chosen in particular from polyols having in particular from 2 to 20 carbon atoms, preferably having from 2 to 10 carbon atoms and preferentially having from 2 to 6 carbon atoms, such as glycerol, propylene glycol, butylene glycol, pentylene glycol, hexylene glycol, dipropylene glycol or diethylene glycol; glycol ethers (in particular having from 3 to 16 carbon atoms), such as mono-, di- or tripropylene glycol ($C_1$-$C_4$)alkyl ethers, mono-, di- or triethylene glycol ($C_1$-$C_4$)alkyl ethers; and their mixtures.

The composition according to the invention can comprise a polyol which is miscible with water at ambient temperature. Such polyols can promote the moisturization of the skin surface on which the composition is applied.

In addition, the composition according to the invention can comprise a monoalcohol comprising from 2 to 6 carbon atoms, such as ethanol or isopropanol.

A composition according to the invention advantageously comprises less than 5% by weight of aqueous phase and in particular of water, with respect to the total weight of the composition. Preferentially, a composition according to the invention is devoid of aqueous phase and in particular is devoid of water.

Adjuvants

The compositions in accordance with the present invention can additionally comprise one or more conventional cosmetic adjuvants chosen from waxes, thickeners, softeners, humectants, opacifiers, stabilizers, emollients, silicones, fragrances, preservatives, active agents, polymers or any other ingredient normally used in the cosmetics and/or dermatological fields.

Of course, a person skilled in the art will take care to choose the above-mentioned optional additional compound or compounds and/or their amounts so that the advantageous properties intrinsically attached to the compositions in accordance with the invention are not, or not substantially, detrimentally affected by the envisaged addition or additions.

According to a specific form of the invention, the compositions according to the invention can additionally comprise insoluble UV screening agents chosen from insoluble organic UV screening agents, inorganic UV screening agents and composite materials comprising an organic or inorganic matrix and at least one inorganic UV screening agent.

Insoluble Uv Screening Agents

The term "insoluble UV screening agent" is understood to mean any UV screening agent capable of being in the form of particles in a liquid fatty phase and in a liquid aqueous phase.

The insoluble organic UV screening agent or agents are preferably present in the compositions according to the invention at a content ranging from 0.1% to 10% by weight and in particular from 0.5% to 5% by weight, with respect to the total weight of the composition.

Mention may be made, among insoluble organic screening agents, of those described in applications U.S. Pat. No. 5,237,071, U.S. Pat. No. 5,166,355, GB 2 303 549, DE 197 26 184 and EP 893 119, in particular methylenebis[(hydroxyphenyl)benzotriazole] derivatives, such as Methylene Bis-Benzotriazolyl Tetramethylbutylphenol, sold in the solid form under the trade name Mixxim BB/100 by Fairmount Chemical or in the micronized form in aqueous dispersion under the trade name Tinosorb M by BASF.

Mention may also be made of the symmetrical triazine screening agents described in U.S. Pat. No. 6,225,467, Application WO 2004/085412 (see compounds 6 and 9) or the document "Symmetrical Triazine Derivatives", IP.COM Journal, IP.COM INC, West Henrietta, N.Y., US (20 Sep. 2004), in particular 2,4,6-tris(biphenyl)-1,3,5-triazines (in particular 2,4,6-tris(biphenyl-4-yl)-1,3,5-triazine) and 2,4,6-tris(terphenyl)-1,3,5-triazine, which is also mentioned in Beiersdorf Applications WO 06/035000, WO 06/034982, WO 06/034991, WO 06/035007, WO 2006/034992 and WO 2006/034985.

Inorganic UV Screening Agents

The inorganic UV screening agents used in accordance with the present invention are metal oxide pigments.

According to a specific form of the invention, the inorganic UV screening agents of the invention are metal oxide particles having an average elementary particle size of less than or equal to 0.5 μm, more preferably between 0.005 and 0.5 μm and more preferably still between 0.01 and 0.1 μm, and preferably between 0.015 and 0.05 μm.

The term "average size" of the particles is understood to mean the parameter D[4,3] measured using a Mastersizer 2000 particle size analyser (Malvern). The light intensity scattered by the particles as a function of the angle at which they are illuminated is converted to size distribution according to the Mie theory. The parameter D[4,3] is measured; this is the average diameter of the sphere having the same volume as the particle. For a spherical particle, reference will often be made to "average diameter".

The term "average elementary size" is understood to mean the size of non-aggregated particles.

They can be chosen in particular from titanium, zinc, iron, zirconium or cerium oxides, or their mixtures, and more particularly titanium oxides.

Such coated or non-coated metal oxide pigments are described in particular in Patent Application EP-A-0 518 773. Mention may be made, as commercial pigments, of the products sold by Kemira, Tayca, Merck and Degussa.

The metal oxide pigments can be coated or non-coated.

The coated pigments are pigments which have been subjected to one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides coated:

with silica, such as the product Sunveil from Ikeda, with silica and iron oxide, such as the product Sunveil F from Ikeda, with silica and alumina, such as the products Microtitanium Dioxide MT 500 SA and Microtitanium Dioxide MT 100 SA from Tayca or Tioveil from Tioxide, with alumina, such as the products Tipaque TTO-55 (B) and Tipaque TTO-55 (A) from Ishihara and UVT 14/4 from Kemira, with alumina and aluminium stearate, such as the products Microtitanium Dioxide MT 100 T, MT 100 TX, MT 100 Z and MT-01 from Tayca, the products Solaveil CT-10 W and Solaveil CT 100 from Uniqema and the product Eusolex T-AVO from Merck, with silica, alumina and alginic acid, such as the product MT-100 AQ from Tayca, with alumina and aluminium laurate, such as the product Microtitanium Dioxide MT 100 S from Tayca, with iron oxide and iron stearate, such as the product Microtitanium Dioxide MT 100 F from the company Tayca, with zinc oxide and zinc stearate, such as the product BR 351 from Tayca, with silica and alumina and treated with a silicone, such as the products Microtitanium Dioxide MT 600 SAS, Microtitanium Dioxide MT 500 SAS or Microtitanium Dioxide MT 100 SAS from Tayca, with silica, alumina and aluminium stearate and treated with a silicone, such as the product STT-30-DS from Titan Kogyo, with silica and treated with a silicone, such as the product UV-Titan X 195 from Kemira, with alumina and treated with a silicone, such as the products Tipaque TTO-55 (S) from Ishihara or UV Titan M 262 from Kemira, with triethanolamine, such as the product STT-65-S from Titan Kogyo, with stearic acid, such as the product Tipaque TTO-55 (C) from Ishihara, with sodium hexametaphosphate, such as the product Microtitanium Dioxide MT 150 W from Tayca, with octyltrimethylsilane, sold under the trade name T 805 by Degussa Silices, with a polydimethylsiloxane, sold under the trade name 70250 Cardre UF $TiO_2SI_3$ by Cardre, anatase/rutile $TiO_2$ treated with a polydimethylhydrosiloxane, sold under the trade name Microtitanium Dioxide USP Grade Hydrophobic by Color Techniques.

The non-coated titanium oxide pigments are sold, for example, by Tayca under the trade names Microtitanium Dioxide MT 500 B and Microtitanium Dioxide MT 600 B, by Degussa under the name P 25, by Wackherr under the name Transparent titanium oxide PW, by Miyoshi Kasei under the name UFTR, by Tomen under the name ITS and by Tioxide under the name Tioveil AQ.

The non-coated zinc oxide pigments are, for example:
those sold under the Z-Cote name by Sunsmart;
those sold under the Nanox name by Elementis;
those sold under the name Nanogard WCD 2025 by Nanophase Technologies.

The coated zinc oxide pigments are, for example:
those sold under the name Zinc Oxide CS-5 by Toshibi (ZnO coated with polymethylhydrosiloxane);
those sold under the name Nanogard Zinc Oxide FN by Nanophase Technologies (as a 40% dispersion in Finsolv TN, $C_{12}$-$C_{15}$ alkyl benzoate);
those sold under the names Daitopersion Zn-30 and Daitopersion Zn-50 by Daito (dispersions in oxyethylenated polydimethylsiloxane/cyclopolymethylsiloxane comprising 30% or 50% of zinc oxides coated with silica and polymethylhydrosiloxane);
those sold under the name NFD Ultrafine ZnO by Daikin (ZnO coated with perfluoroalkyl phosphate and copolymer based on perfluoroalkylethylacrylate as a dispersion in cyclopentasiloxane);
those sold under the name SPD-Z1 by Shin-Etsu (ZnO coated with silicone-grafted acrylic polymer, dispersed in cyclodimethylsiloxane);
those sold under the name Escalol Z100 by ISP (alumina-treated ZnO dispersed in an ethylhexyl methoxycinnamate/PVP-hexadecene copolymer/methicone mixture);
those sold under the name Fuji ZnO-SMS-10 by Fuji Pigment (ZnO coated with silica and polymethylsilsesquioxane);
those sold under the name Nanox Gel TN by Elementis (ZnO dispersed at 55% in $C_{12}$-$C_{15}$ alkyl benzoate with hydroxystearic acid polycondensate).

The non-coated cerium oxide pigments can, for example, be those sold under the name Colloidal Cerium Oxide by Rhône-Poulenc.

The non-coated iron oxide pigments are sold, for example, by Arnaud under the names Nanogard WCD 2002 (FE 45B), Nanogard Iron FE 45 BL AQ, Nanogard FE 45R AQ and Nanogard WCD 2006 (FE 45R) or by Mitsubishi under the name TY-220.

The coated iron oxide pigments are sold, for example, by Arnaud under the names Nanogard WCD 2008 (FE 45B FN), Nanogard WCD 2009 (FE 45B 556), Nanogard FE 45 BL 345 and Nanogard FE 45 BL or by BASF under the name Transparent Iron Oxide.

Mention may also be made of mixtures of metal oxides, in particular of titanium dioxide and cerium dioxide, including the mixture of equal weights of titanium dioxide and cerium dioxide which are coated with silica, sold by Ikeda under the name Sunveil A, and also the mixture of titanium dioxide and zinc dioxide coated with alumina, silica and silicone, such as the product M 261 sold by Kemira, or coated with alumina, silica and glycerol, such as the product M 211 sold by Kemira.

According to the invention, coated or non-coated titanium oxide pigments are particularly preferred.

According to a specific form of the invention, the insoluble screening agents can be composed of composite particles with an average size of between 0.1 and 30 µm and comprising a matrix and an inorganic UV screening agent, the content of inorganic screening agent in a particle ranging from 1% to 70% by weight.

These composite particles can be chosen from spherical composite particles, lamellar composite particles or their mixtures.

The term "spherical" is understood to mean that the particle exhibits a sphericity index, that is to say the ratio of its greatest diameter to its smallest diameter, of less than 1.2.

The term "non-spherical" is understood to mean particles in three dimensions (length, width, thickness or height) for which the ratio of the greatest dimension to the smallest dimension is greater than 1.2. The dimensions of the particles of the invention are evaluated by scanning electron microscopy and image analysis. They comprise particles of parallelepipedal shape (rectangular or square surface), discoid shape (circular surface) or ellipsoid shape (oval surface), characterized by three dimensions: a length, a width and a height. When the shape is circular, the length and the width are identical and correspond to the diameter of a disc, whereas the height corresponds to the thickness of the disc. When the surface is oval, the length and the width correspond respectively to the main axis and the minor axis of an ellipse and the height corresponds to the thickness of the elliptic disc formed by the platelet. When a parallelepiped is concerned, the length and the width can be of identical or different dimensions: when they are of the same dimension, the shape of the surface of the parallelepiped is square; in the contrary case, the shape is rectangular. With regard to the height, it corresponds to the thickness of the parallelepiped.

The spherical and non-spherical screening composite particles used according to the present invention comprise a matrix and an inorganic UV screening agent. The matrix comprises one or more organic and/or inorganic materials.

The inorganic UV screening agent is generally chosen from metal oxides, preferably titanium, zinc or iron oxides or their mixtures and more particularly from titanium dioxide $TiO_2$.

These metal oxides can be provided in the form of particles with an average size generally of less than 200 nm. Advantageously, the metal oxide particles used exhibit an average size of less than or equal to 0.1 µm.

These metal oxides can also be provided in the form of layers, preferably multilayers with an average thickness generally of less than 0.2 µm.

According to a first alternative form, the composite particles comprise a matrix comprising an organic and/or inorganic material, in which matrix particles of inorganic UV screening agent are included. According to this embodiment, the matrix exhibits inclusions and particles of inorganic UV screening agent are placed in the inclusions of the matrix.

According to a second alternative form, the composite particles comprise a matrix made of an organic and/or inorganic material, which matrix is covered with at least one layer of inorganic UV screening agent which can be connected to the matrix using a binder.

According to a third alternative form, the composite particles comprise an inorganic UV screening agent covered with at least one layer of an organic and/or inorganic material.

The matrix can also be formed of one or more organic or inorganic materials. There may then be a continuous phase of materials, such as an alloy, that is to say, a continuous phase in which the materials can no longer be separated, or a non-continuous phase of materials, for example composed of an organic or inorganic material covered with a layer of another different organic or inorganic material.

According to an alternative form, in particular when the spherical composite particles comprise a matrix covered with a layer of UV screening agent, the composite particles can furthermore be covered with an additional coating, chosen in particular from biodegradable or biocompatible materials, lipid materials, such as, for example, surfactants or emulsifiers, polymers and oxides.

Spherical Composite Particles

The inorganic materials which can be used in the matrix of the spherical composite particles according to the present invention can be chosen from the group formed by boron nitride, glass, calcium carbonate, barium sulfate, hydroxyapatite, silica, silicate, magnesium sulfate, magnesium carbonate, aluminium oxide, calcium silicate, calcium phosphate, magnesium oxide, bismuth oxychloride and their mixtures.

The organic materials which can be used to form the matrix are chosen from the group formed by poly(meth)acrylates, polyamides, silicones, polyurethanes, polyethylenes, polypropylenes, polystyrenes, polyhydroxyalkanoates, polycaprolactams, poly(butylene succinate)s, polysaccharides, polypeptides, polyvinyl alcohols, polyvinyl resins, fluoropolymers, waxes, polyesters, polyethers and their mixtures.

Preferably, the matrix of the spherical composite particle comprises a material or a mixture of materials chosen from:
- $SiO_2$,
- polymethyl methacrylate,
- copolymers of styrene and of a $C_1/C_5$ alkyl (meth)acrylate derivative,
- polyamides, such as nylon.

The composite particles in spherical form are characterized by an average diameter of between 100 nm and 30 µm, preferably between 300 nm and 20 µm and more preferably between 500 nm and 10 µm.

According to a first alternative form, the spherical composite particles comprise a matrix comprising an organic and/or inorganic material, in which matrix particles of inorganic UV screening agent are included.

According to this first alternative form, the particles of inorganic UV screening agent are characterized by an average elementary size generally of less than 0.2 µm. Advantageously, the metal oxide particles used exhibit an average elementary size of less than or equal to 0.1 µm.

Mention may be made, as composite particles corresponding to this alternative form, of the products Sunsil TIN 50 and Sunsil TIN 40 sold by Sunjin Chemical. These spherical composite particles with an average size of between 2 and 7 µm are formed of $TiO_2$ encapsulated in a silica matrix.

Mention may also be made of the following particles:
- spherical composite particles with an average size of between 4 and 8 µm, comprising $TiO_2$ and $SiO_2$ and having the trade name Eospoly TR, sold by Creations Couleurs,
- composite particles comprising $TiO_2$ and a styrene/alkyl acrylate copolymer matrix, sold under the name Eospoly UV TR22HB 50 by Creations Couleurs,
- composite particles comprising $TiO_2$ and ZnO and a PMMA matrix and having the trade name Sun PMMA-T50, sold by Sunjin Chemical.

According to a second alternative form, the spherical composite particles comprise a matrix made of an organic and/or inorganic material, which matrix is covered with at least one layer of inorganic UV screening agent connected to the matrix using a binder.

According to this second alternative form, the average thickness of the layer of inorganic UV screening agent is generally approximately ten nanometres. The average thickness of the layer of inorganic UV screening agent is advantageously between $10^{-3}$ and 0.2 µm, preferably between 0.001 and 0.2 µm.

The spherical composite particles used according to the invention have a size of between 0.1 and 30 µm, preferably between 0.3 and 20 µm and more preferentially still between 0.5 and 10 µm.

Mention may be made, among the composite particles which can be used according to the invention, of spherical composite particles comprising $TiO_2$ and $SiO_2$ and having the trade name STM ACS-0050510, supplied by JGC Catalysts and Chemical.

According to a third alternative form, the spherical composite particles comprise an inorganic UV screening agent covered with at least one layer of an organic and/or inorganic material. According to this third alternative form, the particles of inorganic UV screening agent are characterized by an average elementary size generally of between $10^{-3}$ and 0.2 µm. Advantageously, the metal oxide particles used exhibit an average elementary size of between 0.01 and 0.1 µm.

The spherical composite particles used according to the invention have a size of between 0.1 and 30 µm, preferably between 0.3 and 20 µm and more preferentially still between 0.5 and 10 µm.

Non-Spherical Composite Particles

The organic materials which can be used to form the matrix of the non-spherical screening particles are chosen from the group formed by poly(meth)acrylates, polyamides, silicones, polyurethanes, polyethylenes, polypropylenes, polystyrenes, polyhydroxyalkanoates, polycaprolactams, poly(butylene succinate)s, polysaccharides, polypeptides, polyvinyl alcohols, polyvinyl resins, fluoropolymers, waxes, polyesters, polyethers and their mixtures.

Mention may preferably be made, among the organic materials which can be used, of:
- triethoxycaprylylsilane,
- acrylic polymers, such as polymethyl methacrylate and acrylic copolymers comprising other types of monomers, such as styrene,
- polyamides, such as nylon.

The inorganic materials which can be used in the matrix of the non-spherical composite particles are chosen from the group formed by mica, synthetic mica, talc, sericite, boron nitride, glass, calcium carbonate, barium sulfate, hydroxyapatite, silica, silicate, magnesium sulfate, magnesium carbonate, magnesium trisilicate, aluminium oxide, calcium silicate, calcium phosphate, magnesium oxide, bismuth oxychloride and their mixtures. Preferably, these inorganic materials are chosen from:
- silica,
- talc,
- mica,
- alumina.

The inorganic UV screening agent is generally chosen from metal oxides, in particular from titanium, zinc or iron oxides and more particularly titanium dioxide ($TiO_2$).

The non-spherical composite particles of the invention are characterized by three dimensions, of which:
- the smallest is greater than 0.1 µm, preferably 0.3 µm and better still 0.5 µm,
- the greatest is less than 30 µm, preferably 20 µm and better still 10 µm.

The ratio of the greatest dimension to the smallest dimension is greater than 1.2.

The dimensions of the particles of the invention are evaluated by scanning electron microscopy and image analysis.

The non-spherical composite particles which can be used according to the invention will preferably be platelet-shaped.

The term "platelet-shaped" is understood to mean a parallelepipedal shape.

They can be smooth, rough or porous.

The platelet-shaped composite particles preferably exhibit an average thickness of between 0.01 and 10 µm, the average length is generally between 0.5 and 30 µm and the average width is between 0.5 and 30 µm.

The thickness is the smallest of the dimensions, the width is the medium dimension and the length is the greatest of the dimensions.

According to a first alternative form, the composite particles comprise a matrix comprising an organic and/or inorganic material, in which matrix particles of inorganic UV screening agent are included.

According to this first alternative form, the particles of inorganic UV screening agent are characterized by an average elementary size generally of less than 0.2 µm. Advantageously, the metal oxide particles used exhibit an average elementary size of less than or equal to 0.1 µm.

According to a second alternative form, the composite particles comprise a matrix made of an organic and/or inorganic material, which matrix is covered with at least one layer of inorganic UV screening agent which can be connected to the matrix using a binder.

According to this second alternative form, the average thickness of the layer of inorganic UV screening agent is generally approximately ten nanometres. The average thickness of the layer of inorganic UV screening agent is advantageously between $10^{-3}$ and 0.2 µm, preferably between 0.01 and 0.2 µm.

The non-spherical composite particles used according to the invention have a size of between 100 nm and 30 µm, preferably between 0.3 and 20 µm and more preferentially still between 0.5 and 10 µm.

According to a third alternative form, the non-spherical composite particles comprise an inorganic UV screening agent covered with at least one layer of an organic and/or inorganic material. According to this third alternative form, the particles of inorganic UV screening agent are characterized by an average elementary size generally of between $10^{-3}$ and 0.2 µm. Advantageously, the metal oxide particles used exhibit an average elementary size of between 0.01 and 0.1 µm.

Preferably, the inorganic UV screening agent used in the composite particle is chosen from metal oxides, in particular from titanium, zinc or iron oxides and more particularly titanium dioxide ($TiO_2$).

Preferably, the matrix of the composite particle comprises a material or a mixture of materials chosen from:
- $SiO_2$,
- alumina,
- mica,
- an alumina/triethoxycaprylylsilane mixture,
- talc,
- PMMA (polymethyl methacrylate),
- Nylon.

More preferably, the matrix of the composite particle is composed of a material or a mixture of materials chosen from:
- alumina,
- an alumina/triethoxycaprylylsilane mixture,
- talc,
- silica,
- mica.

Mention may also be made, among the composite particles which can be used according to the invention, of the following particles:
- composite particles comprising $TiO_2$ and an alumina matrix, with the trade name Matlake OPA, sold by Sensient LCW,
- composite particles comprising $TiO_2$ and an alumina/triethoxycaprylylsilane matrix, with the trade name Matlake OPA AS, sold by Sensient LCW,
- composite particles comprising ultrafine $TiO_2$ particles deposited on the surface of talc platelets, with the trade name TTC 30, sold by Miyoshi Kasei,
- composite particles comprising ultrafine $TiO_2$ particles deposited on the surface of talc platelets, with the trade name Silseem Mistypearl Yellow, sold by Nihon Koken Kogyo (NKK).

The inorganic UV screening agent or agents are preferably present in the compositions according to the invention at a content, as active material, ranging from 0.1% to 20% by weight and in particular from 0.5% to 15% by weight, with respect to the total weight of the composition.

A person skilled in the art will choose the said active agent or agents according to the effect desired on the skin, hair, eyelashes, eyebrows or nails.

The cosmetic compositions according to the invention have applications in a great number of treatments, in particular cosmetic treatments, of the skin, lips and hair, including the scalp.

Another subject-matter of the present invention consists of the use of the compositions according to the invention as defined above in the manufacture of products for the cosmetic treatment of the skin, lips, nails, hair, eyelashes, eyebrows and/or scalp, in particular care products, anti-sun products and make-up products.

The cosmetic compositions according to the invention can be used, for example, as make-up products.

Assembly

According to another aspect, the invention also relates to a cosmetic assembly comprising:
i) a container delimiting one or more compartment(s), the said container being closed by a closing member and optionally not being leaktight; and
ii) a make-up and/or care composition in accordance with the invention placed inside the said compartment(s).

The container can, for example, be in the form of a pot or a case.

The closing member can be in the form of a lid comprising a cap mounted so as to be able to move by translation or by pivoting relative to the container housing the said make-up and/or care composition(s).

The examples which follow serve to illustrate the invention without, however, exhibiting a limiting nature. In these examples, the amounts of the composition ingredients are given as % by weight, with respect to the total weight of the composition.

EXAMPLES

Evaluation Protocols
In Vivo SPF:
The Sun Protection Factor (SPF) of a product is evaluated according to the International Method published by COLIPA/CTFA SA/JCIA (May 2006).
The Sun Protection Factor is the ratio of the Minimal Erythemal Dose obtained in the presence of product (2 mg/cm$^2$) (MEDp) to the Minimal Erythemal Dose obtained without product (MEDnp).

SPF=MED$p$/MED$np$

The Minimal Erythemal Dose is defined as being the amount of energy necessary to produce the first unambiguously perceptible redness, in the clearly defined outlines, evaluated from 16 to 24 hours after exposure to a solar simulator, at 6 increasing doses of UV radiation (progression of 12%).
The test has to be carried out on at least 10 and no more than 20 subjects, and it has to satisfy the statistical criterion (95% confidence interval falls with the range ±17% mean SPF).
Transparency
The compositions are applied in a proportion of 2 mg/cm$^2$ to an area of 2×2 cm$^2$ delimited on the inside of the forearm, the skin colour of which, characterized by the ITA angle, is between 28 and −30.
The following series of colorimetric measurements were carried out using a Minolta CM-508d spectrocolorimeter:
1°) before application of the composition,
2°) 2 minutes after application,
3°) after wiping with a paper handkerchief (standardized body movements).

The results are expressed in the (L*, a*, b*) system, in which L* represents the luminance, a* represents the red-green axis (−a*=green, +a*=red) and b* represents the yellow-blue axis (−b*=blue, +b*=yellow). Thus, a* and b* express the hue of the skin.
For the evaluation of the intensity of the colouring, the factor of interest is the ΔL* relationship, which reflects the darkening/lightening of the colour: the greater the value of ΔL*, the greater the whitening effect:

Δ$L$*=$L$*bare skin−$L$*skin with product

For the evaluation of the change in the colour of the skin, the factor of interest is ΔE*, which reflects the variation in the colour: the greater the value of ΔE, the greater the modification to the colour in comparison with the initial colour. The colour difference is obtained using the Hunter colour difference formula in the L*, a*, b* colorimetric space:

(Δ$E$*)$^2$=[(Δ$L$*)$^2$+(Δ$a$*)$^2$+(Δ$b$*)$^2$]

where
Δa*=a*bare skin−a*skin with product
Δb*=b*bare skin−b*skin with product

Examples A, B and C

| Ingredients | A* | B | C |
|---|---|---|---|
| Talc Luzenac OO from Luzenac | 38.25 | 48.5 | 38.25 |
| Mica (Cl 77019) Concord 1000 from Sciama | 25 | 25 | 25 |
| Polytetrafluoroethylene Ceridust 9205 F from Clariant | 4 | 4 | 4 |
| Polymethyl methacrylate Micropearl M 100 from Matsumoto Yushi-Seiyaku | 5 | 5 | 5 |
| Butyl Methoxydibenzoyl Hexylbenzoate | 3 | | 3 |
| Octocrylene | 7 | | 7 |
| Ethylhexyl Salicylate | 5 | | 5 |
| C$_{12}$-C$_{15}$ Alkyl benzoate | 5 | | 5 |
| Silica Silylate VM-2270 - Dow Corning | 2.25 | | |
| Titanium Dioxide (and) Aluminium Hydroxide (and) Stearic Acid | | 12 | |
| Silica Silylate Aerosil R972 from Evonik Degussa | | | 2.25 |
| Glycerol | 5 | 5 | 5 |
| Mica (and) Iron Oxides (Cl 77019 + 77491) | 0.5 | 0.5 | 0.5 |

*composition according to the invention

Manufacturing Process
For the Compositions A* and C:
The organic screening agents are heated to 75° C. with magnetic stirring. The aerogel particles of hydrophobic silica: Silica Silylate (composition A*) or silica (composition C), are added and homogenization is carried out with a spatula until a powder is obtained. The fillers and the powder obtained above are introduced into a Backer vessel. Stirring is begun (paddles: 500 rev/min; E-motors: 1000 rev/min) for 10 minutes. It is confirmed that the powder is homogeneous. The glycerol is introduced into the Backer vessel. Stirring is begun (paddles: 500 rev/min; E-motors: 1000 rev/min) for 15 minutes. It is confirmed that the powder is homogeneous. The pearlescent agent is introduced into the Backer vessel. Stirring is begun (paddles: 500 rev/min; E-motors: 1000 rev/min) for 5 minutes. It is confirmed that the powder is homogeneous. The powder is sieved.
For the Formulation B:
The fillers and the Titanium Dioxide (and) Aluminium Hydroxide (and) Stearic Acid are introduced into the Backer vessel. Stirring is begun (paddles: 500 rev/min; E-motors: 1000 rev/min) for 10 minutes. It is confirmed that the powder is homogeneous. The glycerol is introduced into the Backer vessel. Stirring is begun (paddles: 500 rev/min; E-motors: 1000 rev/min) for 15 minutes. It is confirmed that the powder is homogeneous. The pearlescent agent is introduced into the Backer vessel. Stirring is begun (paddles: 500 rev/min; E-motors: 1000 rev/min) for 5 minutes. It is confirmed that the powder is homogeneous. The powder is sieved.
Evaluation of the Colour

| Criteria evaluated | A* | B (with TiO$_2$) | C (with conventional silica) |
|---|---|---|---|
| Feasibility | Yes | Yes | No |
| SPF | 30 | 30 | Cannot be carried out |
| ΔL* before wiping | 6.2 | 11.2 | Cannot be carried out |
| ΔE* before wiping | 8.9 | 17.4 | Cannot be carried out |

-continued

| Criteria evaluated | A* | B (with TiO$_2$) | C (with conventional silica) |
|---|---|---|---|
| ΔL* after wiping | 2.5 | 6.5 | Cannot be carried out |
| ΔE* after wiping | 3.2 | 10.8 | Cannot be carried out |

*composition according to the invention

It is found that, for an equivalent screening system, the anti-sun powder can be produced with a hydrophobic silica aerogel (composition A according to the invention), whereas it cannot be produced with a silica of the state of the art (composition C). It is found that the composition A (silica aerogel+lipophilic organic UV screening agent) and the composition B (hydrophobic silica aerogel+inorganic UV screening agent) can be produced and both exhibit an in vivo SPF of 30. Nevertheless, before wiping and after wiping, the composition A (according to the invention) exhibits a ΔE and a ΔL which are lower than those given by the composition C (state of the art). Thus, the composition according to the invention, A, has a less significant colouring and whitening effect and is therefore more transparent.

Example D According to the Invention (SPF 50)

| Ingredients | Amounts |
|---|---|
| Talc | 10 |
| Mica (CI 77019) | 30 |
| Perlite | 2 |
| Nylon-12 | 2 |
| Polytetrafluoroethylene | 4 |
| Polymethyl methacrylate | 5 |
| Bis-Ethylhexyloxyphenol Methoxyphenyl Triazine | 1 |
| Drometrizole Trisiloxane | 0.5 |
| Diethylamino Hydroxybenzoyl Hexyl Benzoate | 2 |
| Butyl Methoxydibenzoyl Hexylbenzoate | 3 |
| Ethylhexyl Triazone | 1.5 |
| Ethylhexyl Salicylate | 2.5 |
| Octocrylene | 5 |
| Diisopropyl Sebacate | 12 |
| C$_{12}$-C$_{15}$ Alkyl benzoate | 4 |
| Silica Silylate (VM-2270 - Dow Corning) | 5 |
| Silica (and) Titanium Dioxide | 10 |
| Mica (and) Bismuth Oxychloride (and) Carmin (CI 77019 + 77163 + 75470) | 0.5 |

Manufacturing Process: identical to that for the preceding composition A.
Evaluation

| Criteria evaluated | D |
|---|---|
| Feasibility | Yes |
| SPF | 50 |
| ΔL* before wiping | 6.5 |
| ΔE* before wiping | 9.2 |
| ΔL* after wiping | 2.6 |
| ΔE* after wiping | 3.6 |

It is found that the anti-sun powder D can be produced and that it exhibits an SPF of 50. It is found that the composition D exhibits a low ΔE and a low ΔL, before wiping and after wiping. Thus, the composition D according to the invention has a very low colouring and whitening effect and is therefore not very covering.

The invention claimed is:
1. A solid composition comprising, in a cosmetically acceptable medium:
   a) at least one pulverulent phase in an amount of at least 15% by weight based upon the total weight of the solid composition,
   b) at least one lipophilic organic UV screening agent in an amount of 0.1 to 40% by weight based upon the total weight of the solid composition,
wherein the pulverulent phase comprises at least aerogel particles of hydrophobic silica exhibiting a specific surface per unit of weight (S$_w$) ranging from 200 to 1500 m$^2$/g and a size, expressed as volume-average diameter (D[0.5]), of less than 1500 μm in an amount of 0.5 to 15% by weight based upon the total weight of the solid composition.

2. The composition according to claim 1, in the form of a loose or compact powder.

3. The composition according to claim 1, wherein the aerogel particles of hydrophobic silica exhibit a size, expressed as volume-average diameter, ranging from 5 to 25 μm.

4. The composition according to claim 1, wherein the aerogel particles of hydrophobic silica are silica particles modified at the surface with trimethylsilyl groups.

5. The composition according to claim 1, wherein the aerogel particles of hydrophobic silica exhibit a packed density p ranging from 0.04 g/cm$^3$ to 0.10 g/cm$^3$.

6. The composition according to claim 1, wherein the aerogel particles of hydrophobic silica exhibit a specific surface per unit of volume S$_v$ ranging from 5 to 60 m$^2$/cm$^3$.

7. The composition according to claim 1, wherein the aerogel particles of hydrophobic silica have an oil absorption capacity, measured at the wet point, ranging from 5 to 18 ml/g.

8. The composition according to claim 1, wherein the lipophilic organic UV screening agent or agents are chosen from cinnamic derivatives; anthranilates; salicylic derivatives; dibenzoylmethane derivatives; camphor derivatives; benzophenone derivatives;ββ-diphenylacrylate derivatives; triazine derivatives; benzotriazole derivatives; benzalmalonate derivatives; imidazolines; p-aminobenzoic acid (PABA) derivatives; benzoxazole derivatives;
   screening polymers and screening silicones; dimers derived from α-alkylstyrene; 4,4-diarylbutadienes; merocyanine derivatives; and their mixtures.

9. The composition according to claim 8, where the lipophilic organic UV screening agent or agents are chosen from:
   Butyl Methoxy Dibenzoylmethane,
   Octocrylene,
   Ethylhexyl Salicylate,
   n-Hexyl 2-(4-diethylamino-2-hydroxybenzoyl)benzoate,
   Bis-Ethylhexyloxyphenol Methoxyphenyl Triazine,
   Ethylhexyl Triazone,
   Diethylhexyl Butamido Triazone,
   Drometrizole Trisiloxane, and their mixtures.

10. The composition according to claim 1, additionally comprising at least one insoluble UV screening agent chosen from insoluble organic UV screening agents, inorganic UV screening agents and composite materials comprising an organic or inorganic matrix and at least one inorganic UV screening agent.

11. The composition according to claim 1, wherein the pulverulent phase comprises at least one additional filler.

12. The composition according to claim 11, wherein the at least one additional filler is selected from the group consisting of
spherical particles selected from the group consisting of polyamide powders, polymethyl methacrylate microspheres, polytetrafluoroethylene powders and their mixtures, and
the lamellar particles selected from the group consisting of an expanded perlite, a talc, a mica and their mixtures.

13. The composition according to claim 1, comprising at least one liquid fatty phase in an amount of 0.1 to 85% by weight based upon the total weight of the solid composition.

14. The composition according to claim 1, comprising at least one polyol in an amount of 0.1 to 20% by weight based upon the total weight of the solid composition.

15. A cosmetic method for caring for and/or making up human keratinous substances, in particular the skin of the body or of the face or the hair, comprising at least the application, to the surface of the keratinous substance, of at least one composition as defined according to claim 1.

16. The composition according to claim 2, wherein the aerogel particles of hydrophobic silica exhibit a size, expressed as volume-average diameter, ranging from 5 to 25 μm.

17. The composition according to claim 2, wherein the aerogel particles of hydrophobic silica are silica particles modified at the surface with trimethylsilyl groups.

18. The composition according to claim 3, wherein the aerogel particles of hydrophobic silica are silica particles modified at the surface with trimethylsilyl groups.

19. The composition according to claim 2, wherein the aerogel particles of hydrophobic silica exhibit a packed density p ranging from 0.04 $g/cm^3$ to 0.10 $g/cm^3$.

20. The composition according to claim 3, wherein the aerogel particles of hydrophobic silica exhibit a packed density p ranging from 0.04 $g/cm^3$ to 0.10 $g/cm^3$.

21. The composition according to claim 1 wherein the amount of the at least one pulverulent phase is at least 40% by weight based upon the total weight of the solid composition. the amount of the at least one lipophilic organic UV screening agent is 5 to 25% by weight based upon the total weight of the solid composition and the amount of the at least aerogel particles of hydrophobic silica is 1 to 10% by weight based upon the total weight of the solid composition.

* * * * *